US010220019B2

(12) United States Patent
Sun et al.

(10) Patent No.: US 10,220,019 B2
(45) Date of Patent: Mar. 5, 2019

(54) METHOD FOR TREATING PULMONARY FIBROSIS COMPRISING APPLICATION OF DIMETHYLAMINO MICHELIOLIDE

(71) Applicants: Tianjin International Joint Academy of Biotechnology & Medicine, Tianjin (CN); ACCENDATECH, Tianjin (CN)

(72) Inventors: Tao Sun, Tianjin (CN); Yue Chen, Tianjin (CN); Cheng Yang, Tianjin (CN); Honggang Zhou, Tianjin (CN); Huijuan Liu, Tianjin (CN); Yanrong Liu, Tianjin (CN); Jing Wang, Tianjin (CN); Chengyu Zhang, Tianjin (CN); Qiang Zhang, Tianjin (CN); Xiangming Zhang, Tianjin (CN); Yuan Qin, Tianjin (CN); Xueshuang Jing, Tianjin (CN)

(73) Assignees: Tianjin International Joint Academy of Biotechnology & Medicine, Tianjin (CN); ACCENDATECH, Tianjin (CN)

(*) Notice: Subject to any disclaimer, the term of this patent is extended or adjusted under 35 U.S.C. 154(b) by 0 days.

(21) Appl. No.: 15/748,624

(22) PCT Filed: Jan. 28, 2016

(86) PCT No.: PCT/CN2016/072445
§ 371 (c)(1),
(2) Date: Jan. 29, 2018

(87) PCT Pub. No.: WO2017/128163
PCT Pub. Date: Aug. 3, 2017

(65) Prior Publication Data
US 2019/0000798 A1    Jan. 3, 2019

(51) Int. Cl.
A61K 9/00     (2006.01)
A61P 11/00    (2006.01)
A61K 31/365   (2006.01)

(52) U.S. Cl.
CPC .......... A61K 31/365 (2013.01); A61K 9/0019 (2013.01); A61K 9/0053 (2013.01); A61K 9/0073 (2013.01); A61P 11/00 (2018.01)

(58) Field of Classification Search
CPC .......... A61K 9/00; A61K 31/365; A61P 11/00
USPC ....................................................... 514/455
See application file for complete search history.

(56) References Cited

U.S. PATENT DOCUMENTS

| 9,255,078 B2* | 2/2016 | Chen | C07D 307/93 |
| 2013/0109749 A1* | 5/2013 | Chen | C07D 307/93 |
| | | | 514/468 |
| 2016/0367525 A1* | 12/2016 | Chen | A61K 31/365 |

FOREIGN PATENT DOCUMENTS

| CN | 104876899 | 9/2015 |
| CN | 105520933 | 4/2016 |

OTHER PUBLICATIONS

"International Search Report (Form PCT/ISA/210)", dated Nov. 2, 2016, with English translation thereof, pp. 1-4.

* cited by examiner

Primary Examiner — Sabiha N Qazi
(74) Attorney, Agent, or Firm — JCIPRNET

(57) ABSTRACT

The present invention provides an application of a dimethylamino micheliolide for preparing a pharmaceutical product for treating pulmonary fibrosis.

9 Claims, 3 Drawing Sheets

METHOD FOR TREATING PULMONARY FIBROSIS COMPRISING APPLICATION OF DIMETHYLAMINO MICHELIOLIDE

CROSS-REFERENCE TO RELATED APPLICATION

This application is a 371 application of International PCT application serial no. PCT/CN2016/072445, filed on Jan. 28, 2016. The entirety of the above-mentioned patent application is hereby incorporated by reference herein and made a part of this specification.

BACKGROUND OF THE INVENTION

1. Technical Field

The present invention relates to the field of medicinal chemistry, specifically relates to an application of a dimethylamino micheliolide.

2. Description of Related Art

Dimethylamino micheliolide is a derivative of sphaelactone. It is made from natural extract parthenolide as the raw material. In this document, it is referred to as ACT001 for short. Parthenolide is a sesquiterpene lactone compound purified from the herbaceous plants tansy, the characteristics of anti-inflammation, anti-tumor, and anti-platelet aggregation, etc. Currently, studies on ACT001 are mainly focused on the treatment of skin infection, migraine, rheumatism and tumors. The studies have demonstrated that ACT001 and parthenolide have the characteristics of anti-inflammation, anti-tumor, anti-platelet aggregation, inhibiting the proliferation of vascular smooth muscle cells, and suppressing the activity of the osteoclasts, etc. They provide the effect of anti-inflammation through inhibiting the expression of tumor necrosis factor (TNF-α), interleukin-1 (IL-1), IL-12, epoxidase-2 (COX-2), etc.; promote the apoptosis of cancer cells through inhibiting the activation of NF-κB and phosphorylation, and simultaneously inhibit the generation of L-8, and vascular endothelial growth factor (VEGF) to play the role of anti-tumor.

So far, there is no definite report concerning application of ACT001 in pulmonary fibrosis. Cytokines related to pulmonary fibrosis include transforming growth factor-β (TGF-β), epidermal growth factor (EGF), platelet derived growth factor (PDGF), insulin-like growth factors (IGF-1), interleukin (IL), connective tissue growth factor (CTGF), tumor necrosis factor α (TNF-α), matrix metalloproteinases (MMPs), etc. Pulmonary fibrosis is characterized by hyperplasia of fibroblast cells within the lung interstitial resulting in extracellular matrix (ECM) deposition, thus, inhibition of fibroblast cells proliferation is an important step in the development of anti-fibrosis drug.

Difficulty in breathing appears to be the clinical manifestation of pulmonary fibrosis. In the mild stage of pulmonary fibrosis, difficulty in breathing usually occurs during strenuous exercise. In the progressive stage of pulmonary fibrosis, difficulty in breathing occurs even during rest. Progressive dyspnea can appear in patients with severe pulmonary fibrosis. Pulmonary fibrosis can lead to serious consequences causing structural change and loss of function in the normal lung tissues. When the alveoli are highly replaced with fibrous tissues without gas exchange function, the gas exchange ability within the lung is weaken causing oxygen is unable to enter the bloodstream. The patient will then suffer with breathing difficulties, hypoxia, acidosis, disability, and severe cases can eventually lead to death. Pulmonary fibrosis is characterized by hyperplasia of fibroblast cells within the lung interstitial and over-deposition of ECM. The fibrocytes are unable to replace the alveolar cells for gas exchange function and deposition of pulmonary blood causing the lung fail to metabolize hazardous substances within the lung in time which will further lead to alveolar cell damage, forming a vicious circle; the over-deposition of ECM causes the compression of blood capillaries, causing the pulmonary blood is unable to circulate smoothly, leading to deposition of pulmonary blood in the lung. Thus, the blood supply level in the lung is reduced leading to the problems of difficulty in breathing, etc.

Lung diseases caused by pulmonary fibrosis is a disease with high incidence. Since pulmonary fibrosis is caused by a persistent pulmonary injury, once pulmonary fibrosis has developed, it is difficult to cure and will cause a great harm to the patient's health. Currently, there are no efficient drugs to treat pulmonary fibrosis. Anti-inflammatory drugs and/or immuno-suppressants, anti-fibrosis drugs, anticoagulant drugs, lung transplantations, etc. are the main clinical measures for treatment. Commonly-used drugs include glucocorticosteroids, nitroimidazole thiolpyrimidine, cyclosporine, mycophenolate mofetil as well as colchicine, penicillamine, etc. that may influence the formation of collagen. Glucocorticosteroid drugs have a history of being used to treat idiopathic pulmonary fibrosis for over 50 years. Summary of various clinical studies shows that glucocorticosteroids have an efficiency rate of no higher than 16% for treating idiopathic pulmonary fibrosis. Nitroimidazole thiolpurine has being used to treat idiopathic pulmonary fibrosis for over 20 years, its effectiveness remains controversial. Other drugs also have varying degrees of controversy in their clinical effectiveness. Pulmonary fibrosis disease requires extensive care, with high mortality rate, lack of clinical treatment measures, and thus, it is of great demand to develop a novel drug for treating pulmonary fibrosis on the basis of extensive understanding of its pathogenesis.

SUMMARY OF THE INVENTION

The purpose of the present invention is to provide an application of a dimethylamino micheliolide for preparing a pharmaceutical product for treating pulmonary fibrosis.

The present invention provides an application of a dimethylamino micheliolide for preparing a pharmaceutical product for treating pulmonary fibrosis, wherein the dimethylamino micheliolide has a molecular structural formula of:

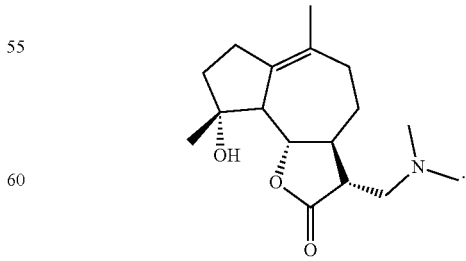

In the aforementioned applications, it includes the application of the dimethylamino micheliolide in preparing the pharmaceutical product to reverse and inhibit level of pulmonary fibrosis, to inhibit over-deposition of pulmonary extracellular matrix and to improve pulmonary blood supply.

In the aforementioned applications, the pharmaceutical product for treating pulmonary fibrosis include the dimethylamino micheliolide, pharmaceutically-acceptable salts, esters, hydrates, or their combinations, and excipients of the dimethylamino micheliolide.

In the aforementioned applications, dosage form of the pharmaceutical product for treating pulmonary fibrosis is selected from tablet, capsule, pill, suppository, aerosol, oral liquid, grain, powder, injection, syrup, vina, tincture, drop, film, or their combinations.

In the aforementioned applications, method of administering the pharmaceutical product for treating pulmonary fibrosis includes: oral, injection, implantation, external use, spray, inhalation, or their combination.

The advantage of the pharmaceutical product for treating pulmonary fibrosis provided by the present invention is: the dimethylamino micheliolide (ACT001) can reverse and inhibit the level of pulmonary fibrosis of the body, inhibit the over-deposition of pulmonary ECM, improve the pulmonary blood supply, and increase the blood-supply quantity to lung so as to relieve the difficulty in breathing, showing a promising therapeutic effect for pulmonary fibrosis. Moreover, the pharmaceutical product not only be easily acceptable by the patients, and with little side effect, low price, with wide origins, easily accessible, and even assist in understanding the pharmaceutical product responses of the patient. In addition, ACT001 will change the existing market structure of the pharmaceutical product for treating pulmonary fibrosis becoming a clinical drug that can be taken long-term, effective in inhibiting pulmonary fibrosis and improving pulmonary function.

ACT001 used according to the present invention is fumarate of ACT001 that is in white powder, provided by ACCENDATECH, batch no. 20131112. The chemical structural formula of ACT001 fumarate is:

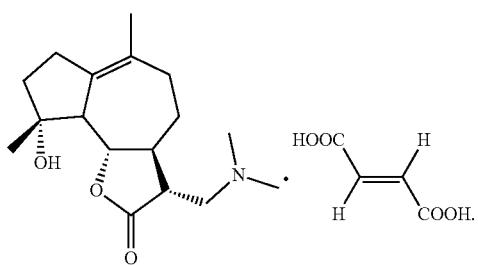

DETAILED DESCRIPTION OF THE INVENTION

Figure 1:
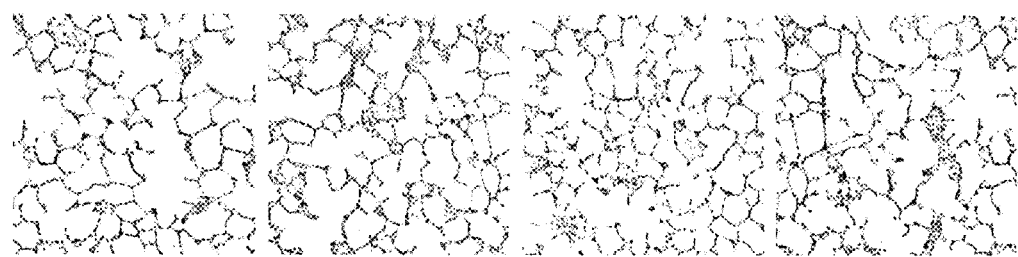
FIG. 1 shows the image of lung tissue section of mice in normal group.

The following will clearly and completely describe the technical solutions in the embodiments according to the present invention in combination with the drawings in the embodiments of the present invention. Obviously, the described embodiments are just the part of rather than all the embodiments according to the present invention. Based on the embodiments of the present invention, all the other embodiments obtained by the person having ordinary skill in the art are covered by the protection scope of the present invention.

The experimental materials used in the present invention and their sources include:

(1) Mice

Kunming mice (male): provided by Laboratory Animal Center of Academy of Military Medical Sciences and Beijing Vital River Laboratory Animal Technology Co., Ltd.

After the arrival of animals, the animals were received by designated person into Mice Feeding Room 2 where is an environment shielded by double corridor, and an "Experimental Animal Receiving Record Form" (BG-017-V00) was filled. The general conditions of the animals were observed upon receiving, and the animals were randomly selected to weight to ensure that the experimental animals are match with the standards of introduction. License No. for using experimental animals: SYXK (Tianjin) 2012-0003.

(2) Testing Samples

ACT001 fumarate: white powder purchased from ACCENDATECH, batch No.: 20131112.

Methyl viologen hydrate: white crystal purchased from J&K Scientific. Manufacturer: J&K Scientific. Brand: J&K. Purity: 98%. Product number: 6045559, MDL: MFCD00150001, CAS No: 1910-42-5.

Storage of the test samples: 4° C.

(3) The Method of Preparing the Drugs and Reagents Used Consisting:

a) Preparation of ACT001 solution: 1 g ACT001 powder was weighed and dissolved in 100 mL 0.9% normal saline solution to prepare 10 mg/mL solution. When it was fully dissolved, it was filter sterilized with 0.22 μm filter for use, and was freshly prepared each time before use. The preparation and the use of the solution should be performed in a sterile biosafety cabinet.

b) Preparation of ethyl viologen hydrate solution: 2 g ethyl viologen hydrate was weighed and dissolved in 100 mL 0.9% normal saline to prepare 20 mg/mL solution. When it was fully dissolved, it was filter sterilized with 0.22 μm filter for use, and was freshly prepared each time before each use. The preparation and the use of the solution should be performed in a sterile biosafety cabinet.

c) Preparation of 10% formalin stationary liquid: 100 ml formalin and 900 ml purified water were mixed evenly.

Embodiment 1—Establishment of Mouse Pulmonary Fibrosis Model and Pharmacodynamics Test of ACT001

Experimental Method and Procedure:

1. Establishment of Mouse Pulmonary Fibrosis Model and Drug Administration Treatment 1.1. Establishment of Mouse Pulmonary Fibrosis Model Randomly divide 36 mice into three groups: normal group, control group (pulmonary fibrosis model group), ACT001 group (administering ACT001 after modeling), and 12 animals per group. Conduct a one-off intragastric administration of 0.15 mL of 0.9% normal saline to each animal in the normal group; and conduct a one-off intragastric administration of 0.15 mL of the ethyl viologen hydrate solution to each animal in the control group and ACT001 group.

1.2 Drug Administration Treatment of Mouse with Pulmonary Fibrosis 3 weeks after modeling, drug treatment was given to the mice. Conduct an intragastric administration of 0.1 mL of 0.9% normal saline to each animal in the normal and control groups, and conduct an intragastric administration of 0.1 mL ACT001 aqueous solution to each animal in the ACT001 group. Once every 2 days.

1.3 Pathological Test of Mouse Pulmonary Fibrosis

At the third week after modeling, the second week after drug administration, and the third week after drug administration, four mice were each taken from the normal group, control group and ACT001 group, sacrificed by breaking their necks, their lung tissues were sampled, after fixing the tissues with 10% formalin for two days, the fixing solution on the surface of the lung tissues was washed away with running water, the lung tissues were then dehydrated with a pathological tissue dehydration machine, the tissues were embed in paraffin, the embedded tissues were sectioned, H.E. staining was conducted and slides were covered before observing the changes of the lung tissues under microscope.

Experimental Results and Evaluation

1) Results of Establishment of Model

Figure 2:
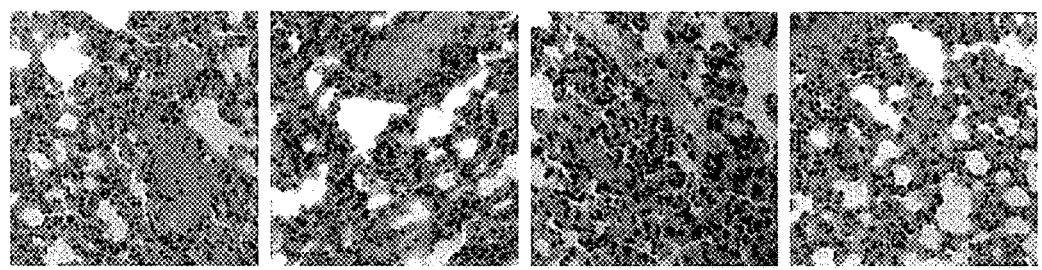
FIG. 2 shows the image of lung tissue section of mice in control group (pulmonary fibrosis model group) at the third week after pulmonary fibrosis model establishment.

As shown in FIG. 1, FIG. 1 is the image of lung tissue section of normal mice. As shown in FIG. 2, FIG. 2 is an image of lung tissue section of mice at the third week after mouse pulmonary fibrosis model establishment. It can be observed from FIG. 2 that significant pulmonary fibrosis appeared in the established model group: deposition of ECM in the pulmonary alveoli and mesenchyme, extensive repair with fibrous tissues, hyperplasia of pulmonary fibers, fibrosis of pulmonary mesenchyme, collagen deposition and structural changes of the pulmonary alveoli.

2) Pharmacodynamics Test of ACT001

Figure 3A:
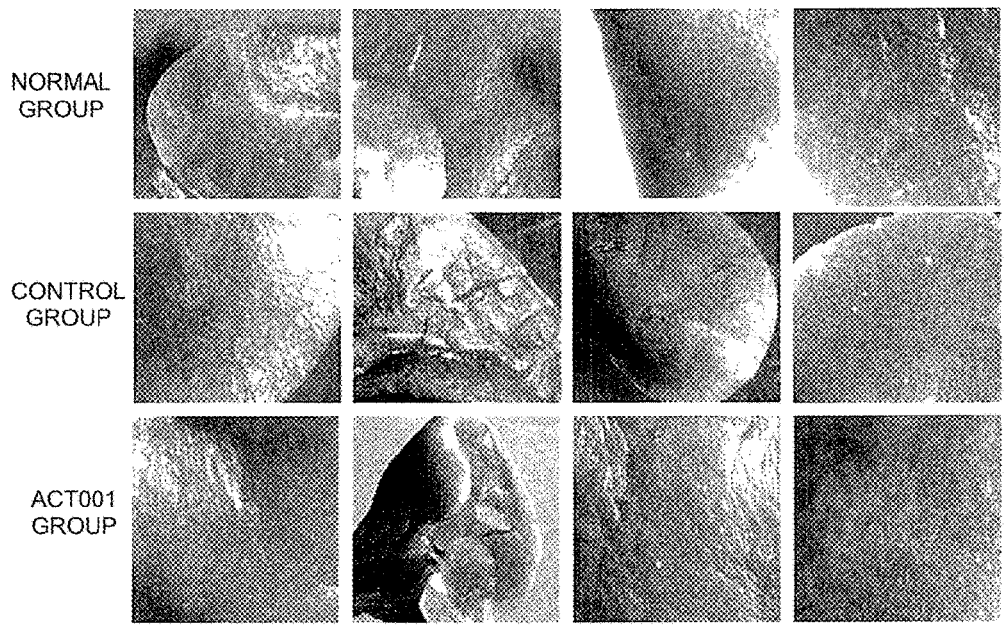
FIG. 3A shows the image of lung tissue morphology of mice in all groups under stereoscopic microscope at the second week after ACT001 administration.

The mice were dissected at the second week after ACT001 administration and the efficacy of ACT001 on pulmonary fibrosis was tested. Lung tissues of the mice were observed after dissection and the results were shown in FIG. 3A, FIG. 3A shows the effect image of mice lung tissues morphology under stereoscopic microscope at the second week after ACT001 administration. It can be known from FIG. 3A that: compared with the control group, lung tissues in the group with ACT001 administration were relatively ruddier, showing significant improvement of blood supply in the lung tissue, the lung tissue was bright red in color, which is equivalent to the tissue appearance of mice from the normal group; however, lung tissue surface of mice from the modeling group without drug administration was dark in color and the surface of the lung tissues was not relatively ruddier. It can be seen that the blood supply in the lung tissues of the mice administered with dimethylamino micheliolide (ACT001) was significantly improved. It can be seen that administration of ACT001 significantly improve the pulmonary blood supply and thus able to relieve the body symptoms of difficulty in breathing such as dyspnea.

When the lungs were observed under stereoscopic microscope, the surface of the lung tissues from the modeling group without drug administration has a pale color appearance, blood vessels at the edge of the lung tissues were fine and scarce, changes appeared in the lung tissues, fibroplasia was observed in the relatively large area of pulmonary parenchyma and the alveolar structures shown significant damage.

Figure 3B:
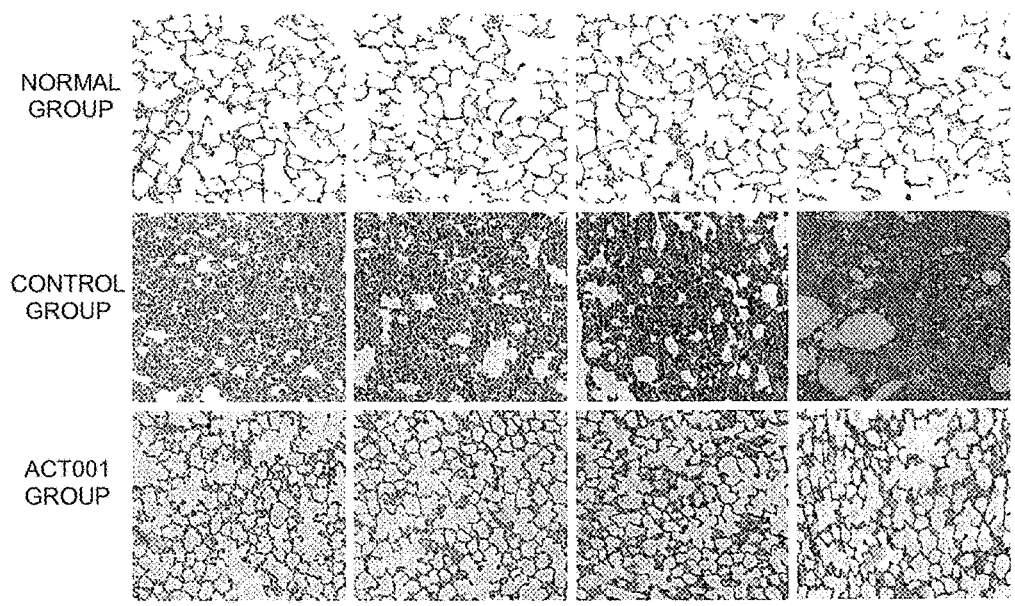
FIG. 3B shows the lung tissue section of mice in all groups at the second week after ACT001 administration.

The lung tissues section of the mice was shown in FIG. 3B, FIG. 3B shows the image of lung tissue section of mice at the second week after ACT001 administration. It can be known from FIG. 3B that: compared with the normal mice, the mice from the control group (i.e., no drug administration) showed significant lung fibrosis after the injection of ethyl viologen hydrate; the ACT001 group with drug administration showed no apparent changes to the lung tissues, phenomenon of fibroplasia in the pulmonary parenchyma was not observed and the alveolar structures were not being damaged; it was a significant improvement for the fibrosis degree of the lung, deposition in the lung interstitials was significantly reduced, and the alveolar structures were restored to normal.

Figure 4A:
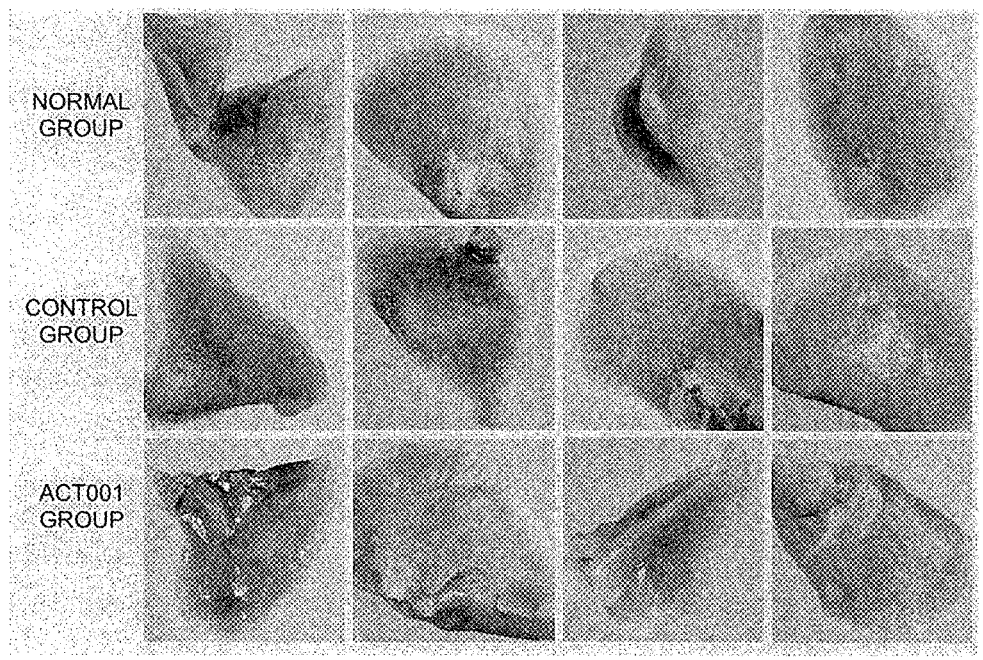
FIG. 4A shows the lung tissue morphology of mice in all groups under stereoscopic microscope at the third week after ACT001 administration.
Figure 4B:
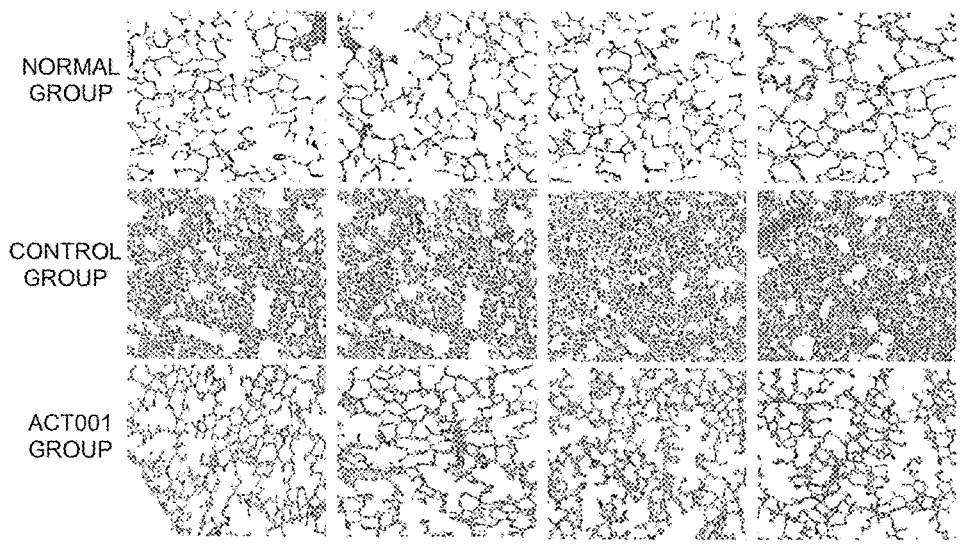
FIG. 4B shows the lung tissue section of mice in all groups at the third week after ACT001 administration.

Images of lung tissues and lung tissues section at the third week after ACT001 administration were shown in FIGS. 4A and 4B, wherein FIG. 4A shows the effect image of mouse lung tissue morphology of mice under stereoscopic microscope at the third week after ACT001 administration and FIG. 4B is an effect image of mice tissue section at the third week after ACT001 administration. It can be known from FIG. 4A and FIG. 4B that: compared with the control group, the ACT001 group with drug administration showed significant improvement in the degree of pulmonary fibrosis, the level of pulmonary fibrosis was significantly reduced, which was equivalent to the appearance of the normal group.

In addition, after 3 weeks of drug administration, body weights of the mice in the normal group, the control group, and the ACT001 group with drug administration were observed and the pulmonary coefficients of each group were calculated. The average body weights of the mice in each group were: the average body weight of mice from the normal group was 49.2352 g, the average body weight of mice from the control group was 45.4575 g, and the average body weight of mice from the ACT001 group with drug administration was 47.576 g. The average lung weights of the mice in each group were: the average lung weight of mice from the normal group was 0.4012 g, the average lung weight of mice from the control group was 0.5983 g, and the average lung weight of mice from the ACT001 group with drug administration was 0.4034 g. According to the formula: pulmonary coefficient=lung wet mass (mg)/body weight (g)*100%, after calculation, the pulmonary coefficients of the mice in each group were: the average of pulmonary coefficient of mice from the normal group was 0.81%, the average of pulmonary coefficient of mice from the control group was 1.32%, and the average of pulmonary coefficient of mice from the ACT001 group with drug administration was 0.85%, respectively. The pulmonary coefficient of the control group was significantly higher than that of the normal group, and there was no significant difference in the pulmonary coefficient of the ACT001 group with drug administration and the pulmonary coefficient of the normal group. Since the pulmonary coefficient represents the degree of pulmonary fibrosis, in relative to the control group, the average pulmonary coefficient of the ACT001 group with drug administration of 0.85%, which was lower by 0.47%, was closed to the average pulmonary coefficient of the normal group, which was 0.81%. Thus, it demonstrated that ACT001 was able to reverse and improve the level of pulmonary fibrosis, improve the over-deposition of ECM, and inhibit the hyperplasia of pulmonary cells with fibrosis.

The embodiments above demonstrate that: ACT001 was able to reverse and inhibit the level of the pulmonary fibrosis, inhibit the over-deposition of the pulmonary ECM, improve the pulmonary blood supply increasing the pulmonary blood flow and relieve the difficulty in breathing, and with the function of treating pulmonary fibrosis.

The descriptions above are just the preferable embodiments according to the present invention and not used to limit the present invention. Any modification, equivalent replacement and/or improvement performed within the spirit and principle of the present invention shall be covered by the protection scope of the present invention.

What is claimed is:

1. A method for treating pulmonary fibrosis, comprising an application of a dimethylamino micheliolide in preparing a pharmaceutical product, wherein the dimethylamino micheliolide has a molecular structural formula of:

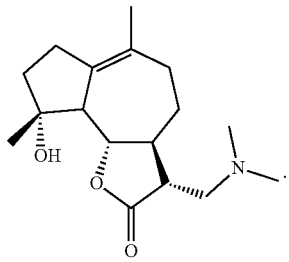

2. The method according to claim 1, comprising an application of the dimethylamino micheliolide in preparing the pharmaceutical product to reverse and inhibit level of pulmonary fibrosis, inhibit over-deposition of pulmonary extracellular matrix, and improve pulmonary blood supply.

3. The method according to claim 1, wherein the pharmaceutical product used to treat pulmonary fibrosis comprising the dimethylamino micheliolide, pharmaceutically-acceptable salts, esters, hydrates or their combinations, and excipients of the dimethylamino micheliolide.

4. The method according to claim 1, wherein dosage form of the pharmaceutical product for treating pulmonary fibrosis is selected from tablet, capsule, pill, suppository, aerosol, oral liquid, gain, powder, injection, syrup, vina, tincture, drop, film, or their combinations.

5. The method according to claim 4, wherein method of administering the pharmaceutical product for treating pulmonary fibrosis comprising: oral, injection, implantation, external use, spray, inhalation, or their combination.

6. The method according to claim 2, wherein dosage form of the pharmaceutical product for treating pulmonary fibrosis is selected from tablet, capsule, pill, suppository, aerosol, oral liquid, grain, powder, injection, syrup, vina, tincture, drop, film, or their combinations.

7. The method according to claim 3, wherein dosage form of the pharmaceutical product for treating pulmonary fibrosis is selected from tablet, capsule, pill, suppository, aerosol, oral liquid, grain, powder, injection, syrup, vina, tincture, drop, film, or their combinations.

8. The method according to claim 6, wherein method of administering the pharmaceutical product for treating pulmonary fibrosis comprising: oral, injection, implantation, external use, spray, inhalation, or their combination.

9. The method according to claim 7, wherein method of administering the pharmaceutical product for treating pulmonary fibrosis comprising: oral, injection, implantation, external use, spray, inhalation, or their combination.

* * * * *